United States Patent [19]

Maier et al.

[11] 4,421,548
[45] Dec. 20, 1983

[54] HERBICIDALLY ACTIVE 2-SUBSTITUTED 5-PENOXYPHENYLPHOSPHONIC ACID DERIVATIVES

[75] Inventors: Ludwig Maier, Arlesheim; Dieter Dürr, Bottmingen, both of Switzerland

[73] Assignee: Ciba-Geigy Corporation, Ardsley, N.Y.

[21] Appl. No.: 334,861

[22] Filed: Dec. 28, 1981

Related U.S. Application Data

[62] Division of Ser. No. 117,167, Jan. 31, 1980, Pat. No. 4,322,375.

[30] Foreign Application Priority Data

Feb. 6, 1979 [CH] Switzerland .......................... 1147/79

[51] Int. Cl.³ ............................................. A01N 57/14
[52] U.S. Cl. ............................................ 71/86; 71/87; 71/76; 260/940; 260/951
[58] Field of Search ...................................... 71/86, 87

[56] References Cited

PUBLICATIONS

Abstract of Japanese Koki Tokkyo Koho JP 82, 14,595, "Chem. Abstracts", vol. 97, (1982), 24007m.

*Primary Examiner*—Anton H. Sutto
*Attorney, Agent, or Firm*—Frederick H. Rabin

[57] ABSTRACT

The present invention relates to novel herbicidal and plant growth-inhibiting 2-substituted 5-phenoxyphenylphosphonic acid derivatives of the formula

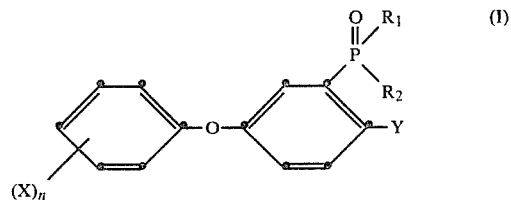

wherein each of $R_1$ and $R_2$ independently is hydroxyl, lower alkoxy, lower alkylthio, alkylamino, dialkylamino, chlorine, benzyloxy or benzylthio, X is halogen or a $-CF_3$, $-NO_2$, $-CN$, $-CONH_2$ or $-CSNH_2$ group, n is 0 to 3, and Y is $-OH$, halogen, $NO_2$, $-CN$, $NH_2$, $-NHCO-R$, $-NHCOOR$ or $-NH-SO_2-R$, wherein R is an unsubstituted or halogenated lower alkyl radical. Preferred compounds are 2-nitro-5-(2'-chloro-4'-trifluoromethylphenoxy)-phenylphosphonic acid and the lower dialkyl esters thereof. The invention also relates to the production of the novel phosphonic acid derivatives, starting from a 3,4-dinitrodiphenyl ether and reacting it with a trialkylphosphite as first step. The invention further relates to herbicidal and plant growth-regulating compositions which contain one of the novel compounds as active component, and also to the use of these compounds and compositions for controlling weeds (also selectively), for inhibiting plant growth and desiccating parts of plants above the soil, as well as for totally destroying existing plant growth.

9 Claims, No Drawings

HERBICIDALLY ACTIVE 2-SUBSTITUTED 5-PENOXYPHENYLPHOSPHONIC ACID DERIVATIVES

This is a division of application Ser. No. 117,167 filed on Jan. 31, 1980 now U.S. Pat. No. 4,322,375.

The present invention relates to novel plant growth-influencing, especially herbicidally active, 2-substituted 5-phenoxyphenylphosphonic acid derivatives, processes for their production, plant growth-influencing (especially herbicidal) compositions which contain these novel phosphonic acid derivatives as active ingredient, and a method for the selective or total control of weeds and of regulating plant growth which comprises the use of these novel compounds.

Chlorinated and unchlorinated 2-nitrophenylphosphonic acids and the sodium salts and ethyl esters thereof have been proposed in German Offenlegungsschrift No. 2 619 841 as active ingredients for compositions for regulating plant growth. Some of the active compounds disclosed in this Offenlegungsschrift were already known from earlier publications, such as "Chemical Communications" 1966, 419; J. Chem. Soc. (C) 1969, 1314; and Tetrahedron Letters 1967 (21), 1987–89. The free 2-nitrophenylphosphonic acid is also known to have bactericidal action.

From the series of the phenoxyphenylphosphonic acids, 3-substituted 4-phenoxyphenylphosphonic acids which can be further substituted in the para-position of the phenoxy moiety have been described in "Organic Phosphorus Compounds", ed. G. M. Kopolapoff and L. Maier, John Wiley & Sons Inc., New York, 1976, Vol. 7, pp. 226–227; but no mention of their activity is made.

The compounds of the present invention, namely 2-substituted 5-phenoxyphenylphosphonic acids and their derivatives, are, however, novel compounds which have been found to possess excellent herbicidal and plant growth-regulating, as well as fungicidal and, in some cases, bactericidal properties. On account of the high phytotoxicity of the active compounds, however, these last mentioned properties cannot well be put to practical use in plant protection.

The novel 2-substituted 5-phenoxyphenylphosphonic acid derivatives of the present invention have the formula I

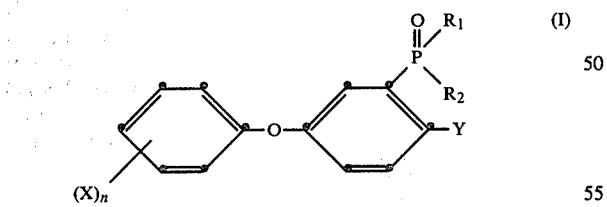

wherein each of $R_1$ and $R_2$ independently is hydroxyl, lower alkoxy, lower alkylthio, alkylamino, dialkylamino, chlorine, benzyloxy or benzylthio, X is halogen or a —$CF_3$, —$NO_2$, —CN, —$CONH_2$ or —$CSNH_2$ group, n is 0 to 3, and Y is —OH, halogen, $NO_2$, —CN, $NH_2$, —NHCO—R, —NHCOOR or —NH—$SO_2$—R, wherein R is an unsubstituted or halogenated lower alkyl radical.

The lower alkyl radicals R, or alkyl moieties of alkoxy, alkylthio and alkylamino groups $R_1$ and $R_2$, contain 1 to 4 carbon atoms, and are accordingly methyl, ethyl, n-propyl, isopropyl, or one of the four possible butyl radicals. Haloalkyl radicals R are e.g. —$CH_2Cl$ and $CF_3$.

Halogen atoms X and Y are chlorine, bromine or iodine, preferably chlorine, atoms.

Particularly interesting and preferred herbicidal compounds are those in which n is 2 and both radicals X (as $X_1$ and $X_2$) are in the ortho- and para-position of the phenoxy radical, and each X independently is $NO_2$, CN, $CF_3$ and halogen, especially chlorine.

Especially preferred compounds are 2-substituted 5-(2'-halogeno-4'-trifluoromethylphenoxy)-phenylphosphonic acid derivatives of the formula IV

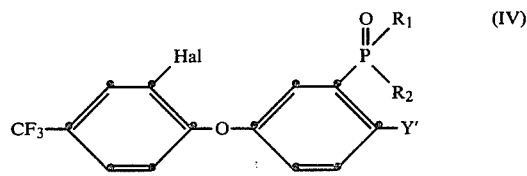

wherein Hal is a halogen atom, especially chlorine, and Y' is a halogen atom, the cyano group and, in particular, the nitro group. Among these compounds, those are in turn preferred in which each of $R_1$ and $R_2$ is lower ($C_1$–$C_3$)alkoxy, such as the dimethyl, diethyl and dipropyl esters of 2-nitro-5-(2'-chloro-4'-trifluoromethylphenoxy)-phenylphosphonic acid.

The novel phosphonic acid derivatives of the formula I are obtained in analogy to the known method of obtaining 2-nitrophenylphosphonic acids (J. Chem. Soc. (C), 1969, 1314), by converting a 1,2-dinitro-5-phenoxybenzene (3,4-dinitrodiphenyl ether) of the formula

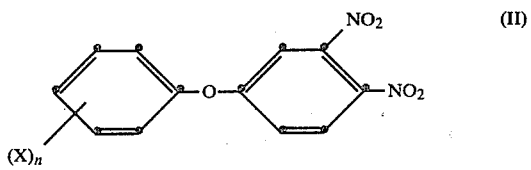

with a trialkylphosphite $P(OR')_3$, wherein R' is lower alkyl, with the removal of one mole of a compound R'—O—N=O, into a dialkyl ester of a 2-nitro-5-phenoxyphenylphosphonic acid of the formula III

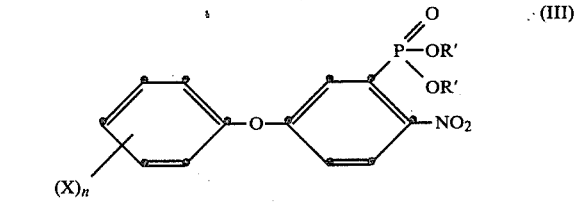

and, if desired, converting this phosphonic acid dialkyl ester radical, in a manner known per se, into the corresponding free phosphonic acid, or into another derivative thereof, in accordance with the definitions of $R_1$ and $R_2$ in formula I. If desired, the remaining nitro group in 2-position can be replaced by another radical Y.

In the above reaction, which is carried out in the temperature angle between 50° and 150° C., preferably between 70° and 120° C., a meta-positioned phosphonic acid ester group results from the nitro group in the meta-position to the phenoxy group, with the removal of one mole of a compound R'—O—N=O, whilst the nitro group in the para-position to the phenoxy group is left unchanged. This is clearly evident from the spectrographic data. The reaction with the trialkylphosphite can be carried out in the absence of a solvent, but preferably in an organic aprotic solvent, such as acetonitrile, benzene or toluene.

The starting materials of the formula II are obtained in accordance with the particulars of European patent application No. 79102225.4. The reaction scheme is as follows:

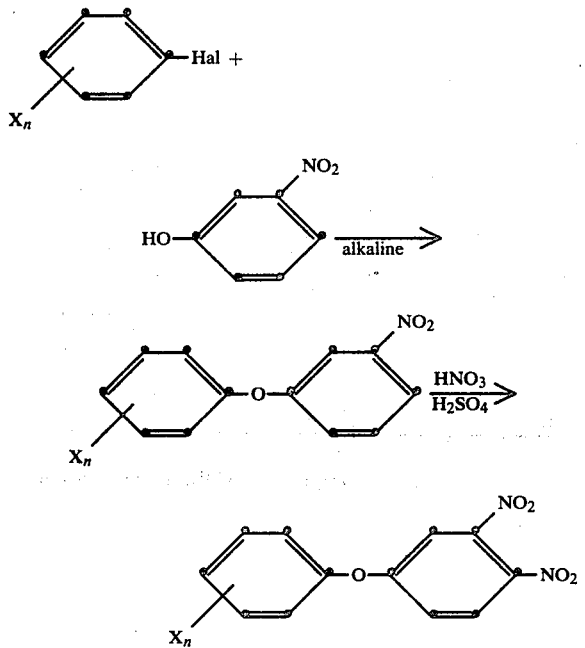

i.e. by nitration of a 3-nitrodiphenyl ether which has been obtained from a halobenzene and 2-nitrophenol.

The nitro group (Y=$NO_2$) which is in the 2-position of the product of the formula III can, if desired, be converted into another group Y. It can be reduced catalytically (Ni or Pd catalysts) with hydrogen to the amino group (—$NH_2$), which can be acylated in turn employing lower fatty acid halides and alkyl chloroformates or alkylsulfonyl halides (Y=—NHCOR, —NH-COOR and —NH—$SO_2$—R).

The amino group can be replaced by halogen or cyano by diazotisation in acid medium with sodium nitrite, and the diazonium salt is reacted in known manner by the method of Sandmeyer with CuCN or a copper halide (CuI), to yield derivatives in which Y is halogen, the cyano group or the hydroxyl group.

The phosphonate ester group can be readily converted into the phosphonyl dichloride ($R_1$, $R_2$=Cl) by treatment with 2 moles of $SOCl_2$ in the presence of dimethyl formamide as catalyst, at elevated temperature (U.S. Pat. No. 4,213,922). By reaction of this dichloride with primary or secondary alkylamines, alcohols, mercaptans or water, it is possible to replace one chlorine atom or both chlorine atoms stepwise by identical or different radicals selected from the groups consisting of alkylamino, dialkylamino, alkoxy, alkylthio, hydroxyl, benzyloxy or benzylthio.

The free phosphonic acid ($R_1$, $R_2$=OH) is also obtained direct from the dialkyl ester by treatment with concentrated hydrochloric acid or ($CH_3$)$_3$SiBr and subsequent hydrolysis of the silyl esters with water.

Both the esters and the free acids and their derivatives of the formula I have an excellent herbicidal activity, both in preemergence and postemergence application.

The following Examples illustrate the production of a number of 2-substituted 5-phenoxyphenylphosphonic acid derivatives of the formula I. Further compounds of the formula I obtained in corresponding manner are listed in the subsequent table.

EXAMPLE 1

2-Nitro-5-(2'-nitro-4'-trifluoromethylphenoxy)-phenylphosphonic acid diethyl ester A mixture of 9 g (24.1 millimoles) of 1,2-dinitro-5-(2'-nitro-4'-trifluoromethylphenoxy)-benzene (m.p. 113°–114° C.) and 4 g (24.1 millimoles) of triethylphosphite, ($C_2H_5O$)$_3$P, is heated to reflux in 50 ml of toluene under nitrogen for 19 hours, and then the solvent is removed by evaporation under reduced pressure. The residue (10.2 g) is purified by column chromatography on silica gel 60 with ethyl acetate/hexane (4:1). First the non-reacted starting material (3.45 g of dinitro derivative) and then the desired phosphonic acid diethyl ester (5.75 g=51.3% of theory) is eluted. The final product is initially in the form of a viscous, reddish yellow oil and is obtained pure by evaporating off the solvent. After standing for some length of time, the oil crystallises to form yellow crystals having a melting point of 72°–74° C. As second fraction, 0.3 g of triethylphosphite is recovered.

Analysis of the final product $C_{17}H_{16}F_3N_2O_8P$ (464.29):

calculated: C: 43.98; H: 3.47; N: 6.03; F: 12.28%; found: C: 43.6; H: 3.6; N: 6.1; F: 12.0%.

$^1$H-NMR (CDCl$_3$): δ1.3 (t,6H, CH$_3$); 4.2 (quin., 4H,OCH$_2$) 7.1–8.4 (m,6H,C$_6$H$_3$) ppm

EXAMPLE 2

2-Nitro-5-(2'-nitro-4'-chlorophenoxy)-phenylphosphonic acid diethyl ester

A mixture of 7.5 g (22.08 millimoles) of 3,4-dinitro-2'-nitro-4'-chlorodiphenyl ether and 3.67 g (22.08 millimoles) of triethylphosphite [($C_2H_5O$)$_3$P] is refluxed in 50 ml of acetonitrile for 19 hours. After removing the solvent by evaporation, the oily black residue (9 g) is chromatographed on a column of silica gel with ethyl acetate/hexane (4:1), affording, in addition to 1.75 g of non-reacted trinitro derivative, 5.8 g (61.0% of theory) of a honey-like reddish oil which crystallises on standing, has a melting point of 76°–78° C., and constitutes the desired final product.

Analysis: $C_{16}H_{16}Cl N_2O_8P$ (430.74)

calculated: C: 44.62; H: 3.75; N: 6.51; Cl: 8.23%; found: C: 44.5; H: 4.0; N: 6.6; Cl: 8.1%.

$^1$H-NMR (CDCl$_3$) δ1.35 (t,6H,CH$_3$); 4.23 (quin. 4H, OCH$_2$) 7.1–8.3 (m,C$_6$H$_3$, 6H) ppm.

EXAMPLE 3

2-Nitro-5-(2'-nitro-4'-trifluoromethylphenoxy)-phenylphosphonic acid

A mixture of 1.85 g of the 2-nitro-5-(2'-nitro-4'-trifluoromethylphenoxy)-phenylphosphonic acid diethyl ester obtained in Example 1, in 20 ml of ethanol, and 40 ml of 20% hydrochloric acid, is refluxed for 24 hours and then evaporated to dryness, affording as residue the monohydrate of the corresponding free phosphonic acid in the form of yellowish brown crystals in quantitative yield. Melting point: 175°–180° C.

Analysis: $C_{13}H_8F_3N_2O_8P.H_2O$ (426.18)

calculated: C: 36.9; H: 2.53; N: 6.57; P: 7.26%; found: C: 37.9; H: 2.5; N: 6.7; P: 7.5%.

EXAMPLE 4

2-Nitro-5-(2'-cyano-4'-trifluoromethylphenoxy)-phenylphosphonic acid

2-Nitro-5-(2'-cyano-4'-trifluoromethylphenoxy)-phenylphosphonic acid diethyl ester (yellowish red oil) is prepared in acordance with the particulars of Example 1, starting from 3,4-dinitro-2'-cyano-4'-trifluoromethyl-diphenyl ether (m.p. 108°–110° C.) and triethylphosphite. Yield: 48%.

A mixture of 1.6 g of this ester and 1.5 ml of $(CH_3)_3SiBr$ is stirred overnight at room temperature and then concentrated. The residue is dissolved in acetone and, after the addition of water, the solution is concentrated, affording 1.2 g (82%) of 2-nitro-5-(2'-cyano-4'-trifluoromethylphenoxy)-phenylphosphonic acid monohydrate with a melting point of 227° C.

Analysis: $C_{14}H_8F_3N_2O_6P.H_2O$ (406.2)

calculated: C: 41.4; H: 2.48; N: 6.9; P: 7.62%; found: C: 41.4; H: 2.4; N: 6.9; P: 7.6%.

EXAMPLE 5

2-Amino-5-(2'-chloro-4'-trifluoromethylphenoxy)-phenylphosphonic acid dimethyl ester 2-Nitro-5-(2'-chloro-4'-trifluoromethylphenoxy)-phenylphosphonic acid dimethyl ester with a melting point of 83° C. is obtained in accordance with the particulars of Example 1, starting from 3,4-di-nitro-2'-chloro-4'-trifluoromethyl diphenyl ether and trimethylphosphite. Yield: 36.6%.

10 g of this compound are then hydrogenated at room temperature in methanol in the presence of Pd on carbon as catalyst. After uptake of 109% of theory of hydrogen, the catalyst is removed by filtration and the filtrate is concentrated, affording 9.2 g (100% of theory) of the above 2-amino compound is the form of a brown oil which, after chromatography on silica gel, becomes a slightly yellow oil.

$^1H$—NMR in $CDCl_3$: δ3.75 (d; $I_{POCH}11,5$; 6H; $OCH_3$); 5.10 (s, 2H, $NH_2$); 6.6–7.7 (m, 6H, $C_6H_3$) ppm.

The following table lists further compounds of the formula

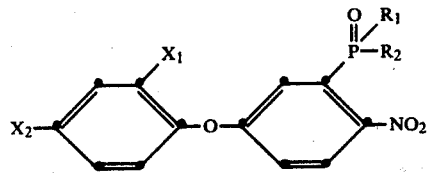

which are obtained in analogous manner.

| Compound | $X_1$ | $X_2$ | $R_1$ and $R_2$ | Physical constants (°C.) |
|---|---|---|---|---|
| 1 | $NO_2$ | $CF_3$ | $OC_2H_5$ | m.p. 72–74° |
| 2 | $NO_2$ | Cl | $OC_2H_5$ | m.p. 76–78° |
| 3 | $NO_2$ | $CF_3$ | OH | m.p. 175–180° (monohydrate) |
| 4 | CN | $CF_3$ | $OC_2H_5$ | yellowish red oil |
| 5 | CN | $CF_3$ | OH | m.p. 227° (monohydrate) |
| 6 | $NO_2$ | $CF_3$ | $OC_3H_7$(iso) | m.p. 93–102° |
| 7 | Cl | $CF_3$ | $OC_2H_5$ | m.p. 61–63° |
| 8 | —$CONH_2$ | $NO_2$ | $OC_2H_5$ | m.p. 137–140° |
| 9 | $CF_3$ | $NO_2$ | $OC_2H_5$ | m.p. 84–88° |
| 10 | Cl | $CF_3$ | $OCH_3$ | m.p. 83° |
| 11 | Cl | $CF_3$ | $OC_3H_7$(iso) | viscous oil |
| 12 | $NO_2$ | Cl | OH | m.p. 170–174° |
| 13 | Cl | $CF_3$ | OH | 2.5 hydrate: m.p. 105–107° |
| 14 | $CF_3$ | $NO_2$ | OH | m.p. 80° (hygroscopic) |
| 15 | Cl | $CF_3$ | —NH—$C_3H_7$iso | m.p. 127–128° |

Further selected compounds of the general formula

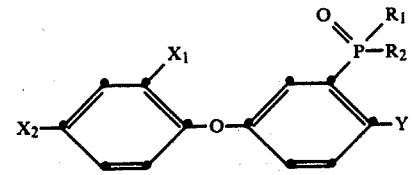

are listed in the following table:

| Compound | $X_1$ | $X_2$ | $R_1$ | $R_2$ | Y | Physical constants (°C.) |
|---|---|---|---|---|---|---|
| 16 | Cl | $CF_3$ | —$N(C_2H_5)_2$ | —$OCH_3$ | $NO_2$ | oil |
| 17 | Cl | $CF_3$ | Cl | Cl | $NO_2$ | |
| 18 | Cl | $CF_3$ | —$NHC_2H_5$ | —$NHC_2H_5$ | $NO_2$ | |
| 19 | Cl | $CF_3$ | —S—benzyl | —S—benzyl | $NO_2$ | |
| 20 | Cl | $CF_3$ | —$N(CH_3)_2$ | —$N(CH_3)_2$ | $NO_2$ | |
| 21 | Cl | $CF_3$ | —$OC_2H_5$ | —S—benzyl | $NO_2$ | |
| 22 | Cl | $CF_3$ | —$OC_2H_5$ | —$N(C_2H_5)_2$ | $NO_2$ | |
| 23 | Cl | $CF_3$ | —$OCH_3$ | —$OCH_3$ | $NH_2$ | oil |
| 24 | Cl | $CF_3$ | —$OC_2H_5$ | —$OC_2H_5$ | $NH_2$ | |
| 25 | Cl | $CF_3$ | —$OCH_3$ | —$OCH_3$ | —$NHCOCH_2Cl$ | oil |
| 26 | Cl | $CF_3$ | —$OC_2H_5$ | —$OC_2H_5$ | —$NHCOCH_2Cl$ | |
| 27 | Cl | $CF_3$ | —$OCH_3$ | —$OCH_3$ | —$NHSO_2CF_3$ | |
| 28 | Cl | $CF_3$ | —$OC_2H_5$ | —$OC_2H_5$ | —$NHSO_2CF_3$ | |
| 29 | Cl | $CF_3$ | —$OCH_3$ | —$OCH_3$ | —OH | |
| 30 | Cl | $CF_3$ | —$OC_2H_5$ | —$OC_2H_5$ | —OH | |

The novel phosphonic acid derivatives of the formula I are compounds which are stable at temperatures below 160° C. and which are soluble in conventional organic solvents.

For use as herbicides or plant growth-regulators, the novel compounds can be employed by themselves or preferably together with suitable carriers and/or other adjuvants in the form of compositions.

Most preferably, the compounds of the formula I are employed as preemergence, and especially as postemergence, herbicides; many of the compounds are translocated in the plant. In low concentrations, the active ingredients act as growth inhibitors of mono- and dicotyledonous plants and also desiccate parts of plants above the soil.

Many of the novel compounds of the formula I, especially those of the narrower formula IV, have low selectivity, but compensate for this by their excellent suitability as post emergence knock-down agents for the rapid and total destruction and desiccation of plant cover and plant populations which are undesirable or are to be replaced.

Such a field of use is e.g. the destruction of convolvulus species in vineyards, where e.g. compound 10 of the table has a 95% effect in a concentration of 2 kg/ha.

A still more important field of use opened up by the rapid and total contact action of the novel compounds, especially those of the formula IV, is the total regeneration of a harvested crop area or of a pasture by the rapid destruction (desiccation) of the entire flora and sowing another crop without ploughing the soil beforehand.

In this "no tillage" system, the soil is no longer ploughed before sowing the new crop. The weed cover or the remaining plants of a previously harvested cereals crop (stubble) are totally destroyed in a few days (to at most 2 weeks) by rapidly acting herbicides instead of by the plough. A new crop is then sown in rows in the perished plant cover by means of special sowing machines.

This method suggests itself in areas which are endangered by erosion through wind and water, and also where it is intended to save on machines, energy and labour, and especially in areas where, after the harvesting of a first crop, the subsequent crop must be quickly gathered in, as in a crop rotation:
wheat→soybean or maize or cotton
grass→soybean or maize or cotton
(pasture or artificial grassland)
soybean stubble→maize
maize stubble→soybean Usually there is used not only one herbicide alone, but a mixture of 3 herbicides. One of the compositions is always a rapid acting herbicide; as such, Paraquat has primarily up to now been used, mixed with e.g. Atrazine or an acetanilide.

Many of the compounds of the present invention, especially those of the formula IV, e.g. compound 10, possess properties which enable them to assume completely the role of Paraquat in the no tillage system mentioned above, without having the disadvantages of this latter (toxicity to warm-blooded animals) to the same extent.

The compositions of the present invention are obtained in known manner by intimately mixing and grinding active ingredients (compounds) of the general formula I with suitable carriers and/or adjuvants, with or without the addition of antifoams, wetting agents, dispersants and/or solvents which are inert to the active substances. The active ingredients can be processed to the following formulations:

solid formulations: dusts, tracking powders, granules (coated granules, impregnated granules and homogeneous granules);

active ingredient concentrates which are dispersible in water: wettable powders, pastes, emulsions, emulsion concentrates; liquid formulations: solutions.

The concentrations of active ingredient in the compositions of this invention are between 1 and 80 percent by weight, and can be diluted before use to lower concentrations of about 0.05 to 1 percent by weight.

The compositions of the present invention can be mixed with other biocidal active substances or compositions. Thus in addition to containing the compounds of the general formula I, the compositions of the invention can also contain e.g. insecticides, fungicides, bactericides, fungistatic agents, bacteriostatic agents, nematocides or further herbicides, in order to broaden the activity spectrum.

The following Examples will serve to illustrate in more detail the preparation of solid and liquid formulations containing the compounds of the invention. Throughout, parts and percentages are by weight.

Granules

The following substances are used to formulate 5% granules:
5 parts of one of the active ingredients of the formula I,
0.25 parts of epichlorohydrin,
0.25 parts of cetyl polyglycol ether,
3.50 parts of polyethylene glycol,
91 parts of kaolin (particle size 0.3–0.8 mm).

The active ingredient is mixed with epichlorohydrin and dissolved with 6 parts of acetone, and the polyethylene glycol and cetyl polyglycol ether are then added. The resultant solution is sprayed on kaolin and subsequently evaporated in vacuo.

Wettable Powder

The following constituents are used to formulate (a) a 70% and (b) a 10% wettable powder:
(a)
70 parts of 2-nitro-5-(2'-chloro-4'-trifluoromethylphenoxy)-phenylphosphonic acid diethyl ester,
5 parts of sodium dibutylnaphthalenesulfate,
3 parts of naphthalenesulfonic acid/phenolsulfonic acid/formaldehyde condensate (3:2:1),
10 parts of kaolin,
12 parts of Champagne chalk;
(b)
10 parts of 2-nitro-5-(2'-chloro-4'-trifluoromethylphenoxy)-phenylphosphonic acid,
3 parts of a mixture of the sodium salts of saturated fatty alcohol sulfates,
5 parts of naphthalenesulfonic acid/formaldehyde condensate,
83 parts of kaolin.

The respective active ingredient is applied to the corresponding carriers (kaolin and chalk) and then these are mixed and ground, to yield wettable powders of excellent wettability and suspension powder. By diluting these wettable powders with water it is possible to obtain suspensions containing 0.1 to 80% of active ingredient. These suspensions are suitable for controlling weeds in cultivations of plants.

Paste

The following substances are used to formulate a 45% paste:
45 parts of 2-nitro-5-(2'-chloro-4'-trifluoromethylphenoxy)-phenylphosphonic acid dimethyl ester or another active ingredient of the formula I,
5 parts of sodium aluminium silicate,
14 parts of cetyl polyglcol ether with 8 moles of ethylene oxide, 1 part of oleyl polyglycol ether with 5 moles of ethylene oxide,
2 parts of spindle oil,
10 parts of polyethylene glycol,
23 parts of water.

The active ingredient is intimately mixed with the additives in appropriate devices and ground. By diluting the resultant paste with water, it is possible to prepare suspensions of the desired concentration.

Emulsifiable Concentrate

The following ingredients are mixed to formulate a 25% emulsion concentrate:
25 parts of 2-nitro-5-(2'-nitro-4'-trifluoromethylphenoxy)-phenylphosphonic acid diisopropyl ester,
5 parts of a mixture of nonylphenolpolyoxyethylene and calcium dodecylbenzenesulfonate,
15 parts of cyclohexanone,
55 parts of xylene.

This concentrate can be diluted with water to give emulsions in suitable concentrations of e.g. 0.1 to 10%. Such emulsions are suitable for controlling weeds in cultivations of plants.

The following test methods are employed to establish the usefulness of the compounds of the formula I as pre-emergence and post-emergence herbicides.

Pre-emergence herbicidal action (inhibition of germination)

In a greenhouse, immediately after sowing the test plants in seed dishes, the surface of the soil is treated with an aqueous dispersion of the active ingredients, obtained from a 25% emulsifiable concentrate or from a 25% wettable powder with active ingredients which, on account of their insufficient solubility, cannot be formulated to an emulsifiable concentrate. Four different concentration series were used, corresponding to 4, 2, 1 and 0.5 kg of active substance per hectare respectively. The seed dishes are kept in the greenhouse at 22°–25° C. and 50–70% relative humidity. The test is evaluated 3 weeks later according to the following rating:

1 = plants have not germinated or are totally withered
2–3 = very strong action
4–6 = average action
7–8 = slight action
9 = no action (as untreated control)
- = plant not tested in corresponding active substance concentration.

Whilst e.g. compounds 6 and 7 of the table achieve a rating between 1 and 4 when applied to Sinapis, Setaria and Stellaria in a concentration of 4 kg/ha, the comparison compounds known from German Offenlegungsschrift No. 2 619 841, i.e. 2-nitrophenylphosphonic acid and 2-nitro-5-chlorophenylphosphonic acid diethyl ester, have no herbicidal action at all (rating 9), and 2-nitrophenylphosphonic acid diethyl ester had unsatisfactory ratings of 6 to 9.

Post-emergence herbicidal action (Contact herbicide):

A large number (at least 7) of weeds and cultivated plants, both mono- and dicotyledonous, are sprayed after emergence in the 4- to 6-leaf stage with an aqueous active ingredient emulsion in concentrations of 0.06, 0.125, 0.25 and 0.5 kg of active ingredient per hectare and kept at 24°–26° C. and 45–60% relative humidity. The test is evaluated at least 15 days after treatment in accordance with the same rating employed in the pre-emergence test.

Both in the preemergent and postemergent test, the tested compounds, e.g. compounds 3, 6, 7 and 10 of the table act very well on mono- and dicotyledonous weeds and in some cases have good selectivity in soybeans, cotton and cereal species, including rice and maize. Compound 7 has in particular also outstanding selectivity in rice at concentrations of 1 to 2 kg/ha (ratings between 7 and 9) while almost entirely destroying the weeds Echinochloa, Cyperus, Ammania indica and Rotala indica (ratings 1 to 3).

Of the three comparison compounds of German Offenlegungsschrift 2 619 841 referred to above, only 2-nitro-5-chlorophenylphosphonic acid diethyl ester exhibited weak herbicidal action without perceptible selectivity.

What is claimed is:

1. A method of controlling weeds in crops of monocotyledonous or dicotyledonous cultivated plants which comprises applying thereto, either prior to emergence of said plants or after emergence of said plants, in an amount sufficient to destroy said weeds but insufficient to cause harm to said cultivated plants, a compound of the formula

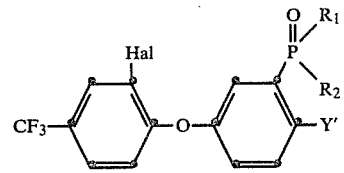

wherein Hal is chlorine, bromine or iodine,
each of $R_1$ and $R_2$ is hydroxy, lower alkoxy, lower alkylthio, (lower alkyl) amino, di(lower alkyl) amino, chlorine, benzyloxy or benzylthio, and
Y' is halogen, nitro or cyano.

2. A method according to claim 1 wherein, in the compound, Hal is chlorine.
3. A method according to claim 2 in which Y' is nitro.
4. A method according to claim 3 in which each of $R_1$ and $R_2$ is $C_1$–$C_3$ alkoxy.
5. The method according to claim 4 in which the compound is 2-nitro-5-(2'chloro-4'-trifluoromethylphenoxy)-phenylphosphonic acid dimethyl ester.
6. A method according to claim 2 in which Y' is chlorine.
7. The method according to claim 6 in which the compound is 2-chloro-5-(2'-chloro-4'trifluoromethylphenoxy)-phenyl-phosphonic acid dimethyl ester.
8. A herbicidal composition which comprises, as active component, a herbicidally effective amount of a compound of the formula

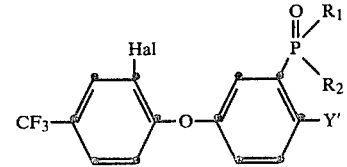

wherein Hal is chlorine, bromine or iodine,
each of $R_1$ and $R_2$ is hydroxy, lower alkoxy, lower alkylthio, (lower alkyl) amino, di(lower alkyl) amino, chlorine, benzyloxy or benzylthio, and
Y' halogen, nitro or cyano.

9. A composition according to claim 8 wherein, in the compound,
each of $R_1$ and $R_2$ is hydroxy or lower alkoxy, and
Y' is nitro.

* * * * *